US00PP32361P2

(12) United States Plant Patent
Hansen

(10) Patent No.: US PP32,361 P2
(45) Date of Patent: Oct. 20, 2020

(54) ***ACHILLEA* PLANT NAMED 'FIREFLY AMETHYST'**

(50) Latin Name: ***Achillea* hybrid**
Varietal Denomination: Firefly Amethyst

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/602,657

(22) Filed: Nov. 15, 2019

(51) Int. Cl.
*A01H 5/02* (2018.01)
*A01H 6/14* (2018.01)

(52) U.S. Cl.
USPC ..... Plt./263.1

(58) Field of Classification Search
USPC ..... Plt./263.1

CPC ... A01H 5/02; A01H 5/00; A01H 6/14; A01H 6/04; A01H 6/06; Y02A 40/138
See application file for complete search history.

(56) References Cited

PUBLICATIONS

Four Star Plugs & Liners from Four Star, Michigan 2019 retrieved on May 18, 2020, retrieved from the Internet at https://cdn.shopify.com/s/files/1/1537/5553/files/2020FourStarPriceList.pdf, pp. 1-2, 13. (Year: 2019).*

* cited by examiner

*Primary Examiner* — June Hwu

(57) ABSTRACT

A new and distinct Yarrow, *Achillea* plant named 'Firefly Amethyst', with billowy habit, dark green, moderately-dissected foliage and large, bright lavender-pink florets that lighten to light pink on heavily-branched compound corymbs, narrow, dark green, fern-like foliage; tall, stiff, heavily branched peduncles with bright lavender-pink florets that lighten to light to very pale lavender, beginning in late June and continuing for about seven weeks and repeating if deadheaded. The new plant is useful for landscaping, as a specimen or en masse and as a cut flower.

1 Drawing Sheet

Botanical designation: *Achillea* hybrid.
Cultivar denomination: 'Firefly Amethyst'.

STATEMENT REGARDING PRIOR DISCLOSURES UNDER 37 CFR 1.77(b)(6)

The first public disclosure of the claimed plant, in the form of a sale, was made by Walters Gardens, Inc. on Apr. 1, 2019. Prior to that, on Dec. 1, 2018 the claimed plant was displayed as a photograph with a brief description on a website operated by Walters Gardens, Inc., followed by listing with a photograph and brief description in the Walters Gardens 19-20 Catalog circulated on May 29, 2019. Walters Gardens, Inc. obtained the plant and all information relating thereto, from the inventor. No plants of *Achillea* 'Firefly Amethyst' have been sold, in this country or anywhere in the world, nor has any disclosure of the new plant been made, more than one year prior the filing date of this application, and such sale or disclosure within one year was either derived directly or indirectly from the inventor.

BACKGROUND OF THE PLANT

The present invention relates to the new and distinct yarrow herein also referred to as *Achillea* 'Firefly Amethyst', by the cultivar name, 'Firefly Amethyst', or as the new plant. The new plant was selected by the inventor as a single seedling resulting from a self-pollination of a proprietary, unreleased, unnamed seedling known only by the breeder code 13-3-9 (not patented) in research facility of a wholesale perennial grower based in Zeeland, Mich., USA.

The cross was performed on Jun. 23, 2014 and the seeds from this cross were collected on Sep. 23, 2014. The single seedling was then isolated and compared in subsequent years to other Yarrow and subsequently found to be different from all cultivars known to the discoverer and eventually given the breeder code 14-67-2.

Asexual propagation at the same nursery in Zeeland, Mich., USA by shoot tip cuttings and division since August of 2016 has shown 'Firefly Amethyst' to be stable and reproduce true to type in successive generations.

SUMMARY OF THE PLANT

*Achillea* 'Firefly Amethyst' has not been observed in all possible environmental conditions. The phenotype may vary slightly with changes in environments such as light intensity, fertility, water availability, etc. without, however any variation in genotype.

*Achillea* 'Firefly Amethyst' is distinct from all cultivars known to the inventor in the following traits:

1. Billowy habit about 55 cm tall and 90 cm wide;
2. Dark green moderately dissected foliage;
3. Heavily-branched peduncles with broad clusters of inflorescences;
4. Large, bright lavender-pink florets that lighten to very pale lavender;
5. Sturdy stems withstand wind and rain;
6. Long flowering period beginning late June and continuing for about seven weeks;
7. Repeat flowering if deadheaded.

Plants of *Achillea* 'Firefly Amethyst' are most similar to 'Balvinolet' U.S. Plant Pat. No. 25,750, 'Lilac Beauty' (not patented), 'Love Parade' (not patented) and 'Wonderful Wampee' U.S. Plant Pat. No. 18,760. 'Balvinolet' is smaller in habit, both shorter and narrower than the new plant, and the ray florets are more reddish-purple when initially open and do not lighten as much as the new plant with maturity. 'Lilac Beauty' is similar in size, but the ray floret color is a much paler lavender. 'Love Parade' has larger florets with less color changing in the ray petals and less branching habit. 'Wonderful Wampee' has floret colors that are a softer pinkish-lavender. The parent selection has an upright narrow habit with ray florets that are more reddish purple.

BRIEF DESCRIPTION OF THE DRAWINGS

The color drawings illustrate the overall characteristics of *Achillea* 'Firefly Amethyst' as a two-year-old plant in a full-sun trial garden in Zeeland, Mich. The colors are as true as reasonably possible given the technology available. The color values may vary slightly depending on light intensity and quality.

DETAILED BOTANICAL DESCRIPTION

Figure 1:
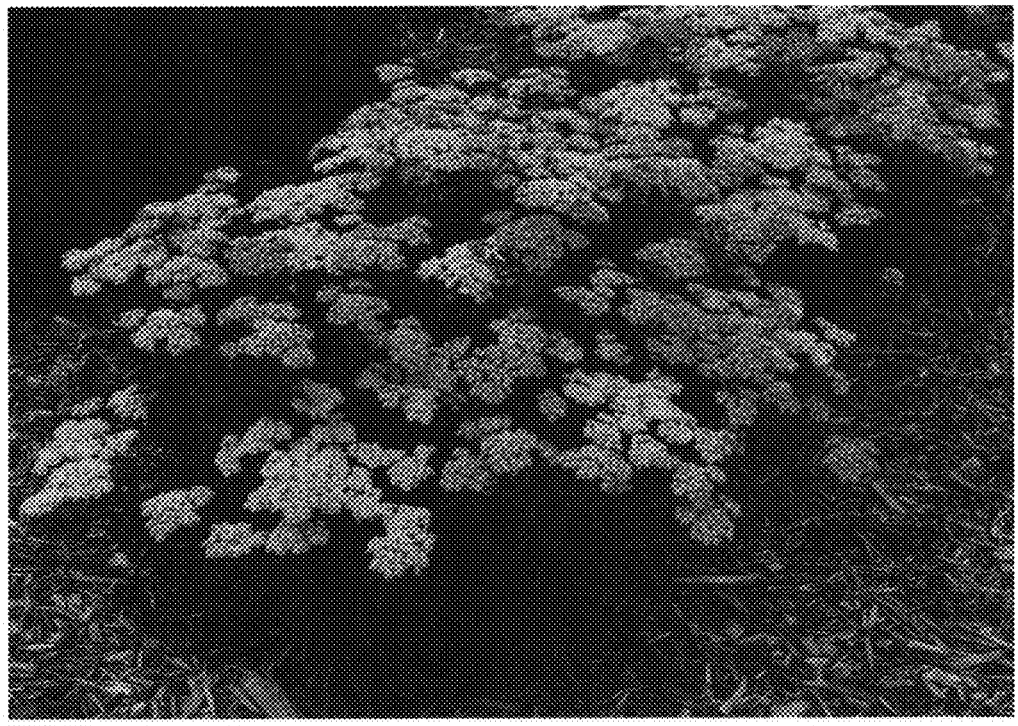
FIG. 1 shows the new plant in a trial facility.
Figure 2:
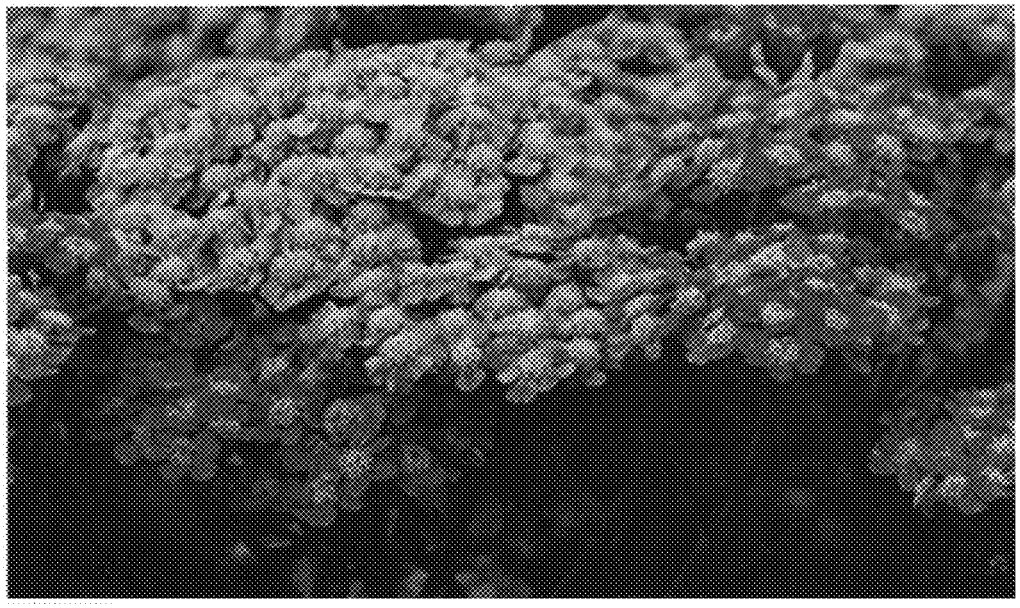
FIG. 2 shows a close-up of the inflorescences of the new plant.

The following description of the new plant is based on a three-year-old plant growing in a full-sun trial garden in Zeeland, Mich., USA. Environmental conditions for the growing season daytime temperatures range between 12-30° C., and night temperatures range between 6-19° C. Except for ordinary dictionary color usage, color references are according to The Royal Horticultural Society Colour Chart, 2015 edition.

Parentage: Female or seed parent 13-9-3; male or pollen parent 13-9-3;

Asexual propagation: Shoot tip cuttings, about 10 to 14 days to initiate roots; time to finish as #1 field grown size about 9 months;

Plant habit: Dense axillary branches; upright, heavily-branched, herbaceous, winter-hardy, perennial mound; up to 55.0 cm tall and 90.0 cm wide; average about 48.0 cm tall and about 69.0 cm across;

Leaves: Alternate; canescent; pinnatifid with lobules moderately incised; lanceolate; acute apex; base attenuate; sessile except proximal leaves; micro-lanulose abaxial and glabrous adaxial; up to about 12.2 cm long and about 3.3 cm wide with individual lobes to about 9.0 mm wide and about 18.0 mm long; average size about 11 cm long and 2.8 cm wide;

Leaf color: Young expanding leaves adaxial lobes nearest RHS 138A and midrib nearest RHS 155A, abaxial lobes nearest RHS 155A and midrib nearest blend between RHS 146C and RHS 145C; mature leaves adaxial lobes nearest RHS 137A and midrib blend between RHS 145D and RHS 155D, abaxial lobes nearest RHS 137A and midribs nearest RHS 146D;

Foliar fragrance: Slight herbal;

Veins: Pinnate; only adaxial and abaxial midrib obvious; abaxial midrib costate, adaxial midrib flat; adaxial sparsely lanulose, abaxial lanulose;

Petiole: Channeled; lanulose; to 2.0 cm long and 4.0 mm wide at base; color nearest RHS 146C;

Stems: Upright; cylindrical; lanulose to micro-pubescent; longitudinally ridged in distal portion; color nearest RHS 137B proximally, distally striped RHS 137B and RHS 146D;

Inflorescence: Radiate; composite consisting of about five to rarely six ray and about 50 disk florets; on heavily branched terminal stems; individual inflorescence about 13.5 mm diameter, about 10.0 mm tall from bottom of involucral bracts to top of center disk tepals; disk about 5.5 mm across; attitude mostly upright; producing branched stems with about 300 inflorescences per stem forming flat-topped compound branched corymb; average size about 12.0 cm across; flowering in upper 8.0 cm and 12 cm across; branches to about 42.0 cm long and 3.0 mm diameter at base;

Receptacle: About 3.0 mm tall; color nearest RHS 148C;

Inflorescence fragrance: Not detected;

Phyllaries: About 20 in two whorls; lanceolate; acute apex; truncate base; margin entire and ciliate; outer or lower set about 2.5 mm long and 1.5 mm across, inner set about 5.0 mm long and 2.0 mm across; glabrous adaxial, pubescent abaxial; tightly adpressed against ray petals;

Phyllary color: Adaxial and abaxial nearest RHS 137B with midrib and margin nearest RHS 155C;

Bristles: Membranous; numerous; about 4.0 mm long and 0.5 mm across; color nearest RHS 155D;

Flowering period: Late June, for about seven weeks and repeating if deadheaded;

Inflorescence longevity: 4 to 6 days;

Inflorescence buds: With ray florets still erect 7.0 mm tall and 4.0 mm across; ovoid;

Inflorescence bud color: Ray florets while still upright exposed abaxial petal color nearest RHS N82B; phyllaries color nearest RHS 137B with midrib and margin nearest RHS 155C;

Pedicel: Cylindrical; lanulose; strong; upright attitude; up to 14.0 mm long and 1.0 mm diameter; average about 8.0 mm long and 0.8 mm diameter;

Pedicel color: Color nearest RHS 137B;

Ray florets: Imperfect; pistillate; typically about five per inflorescence, rarely six; with style about 2.5 mm long and split stigma;

Ray floret ligule: Rounded with basal claw; apex rounded, emarginate with two notches about 0.5 mm deep, margin entire; base claw, attenuate; opening to a 90° angle; glabrous adaxial and adaxial; about 6.0 mm long and about 6.0 mm wide; basal claw about 2.0 mm long and about 1.0 mm across;

*Young ray floret ligule color when first flat*.—Adaxial nearest RHS N81A, abaxial nearest RHS N82B and base nearest RHS 138A.

*Mature ray floret ligule color*.—Adaxial nearest RHS N75D; abaxial between nearest RHS 76D and RHS 76C.

*Ray floret ligule color before dehiscing*.—Adaxial nearest RHS NN155C with light proximal blush of nearest RHS 76D to RHS 76C; abaxial nearest RHS NN155D with faint proximal blush of nearest RHS 76D.

*Style*.—Cylindrical; about 2.0 mm long and 0.2 mm diameter; exserted; color nearest RHS 202A.

*Stigma*.—Bifid; about 0.5 mm long and 0.2 mm diameter; color nearest RHS NN155A initially becoming nearest RHS 202D.

Disk florets: About 50 per capitulum; tubular; glabrous; consisting of five tepals, staminal tube and pistil; size about 6.0 mm long by 1.5 mm wide at apex;

*Tepals*.—Five; linear; fused in basal 5.0 mm; apex acute; margin entire; 6.0 mm long and 0.5 mm wide at fusion.

*Tepal color*.—Initially nearest RHS 69D adaxial and abaxial; at maturity nearest RHS NN155A.

*Staminal tube*.—Made up of five adnate stamens; about 4.0 mm long.

*Filaments*.—Cylindrical; about 1.0 mm long and 0.1 mm diameter; color nearest RHS NN155A.

*Anther*.—About 1.0 mm long; color nearest RHS 17B.

*Pollen*.—Fine, round, closest to RHS 17A.

*Style*.—Bifid; cylindrical; exserted; about 4.0 mm long and 0.2 mm diameter; color proximally nearest RHS NN155A and distally nearest RHS N186A.

*Stigma*.—Bifid; reflexing as it matures; about 1.5 mm long; color nearest RHS N186A.

Seed: Flattened deltoid; acute apex and truncate base; surface glabrous; about 2.0 mm long and 0.7 mm across base;

Seed color: Between RHS 165A and RHS 165B in center and RHS 161D around edges;

*Achillea* 'Firefly Amethyst' is tolerant of winter temperatures as low as −35° C. and summer temperatures as high as 38° C. It is not known to be tolerant of diseases and pest that are common to other *Achillea* cultivars.

I claim:

1. A new and distinct cultivar of *Achillea* plant named 'Firefly Amethyst' as described and illustrated.

* * * * *